US00PP08315P

United States Patent [19]

Drewlow

[11] Patent Number: Plant 8,315

[45] Date of Patent: Jul. 20, 1993

[54] IMPATIENS PLANT NAMED ESCAPADE

[75] Inventor: Lyndon W. Drewlow, Ashtabula, Ohio

[73] Assignee: Mikkelsens, Inc., Ashtabula, Ohio

[21] Appl. No.: 858,394

[22] Filed: Mar. 26, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Assistant Examiner*—Erich Veitenheimer

*Attorney, Agent, or Firm*—Foley & Lardner

[57] ABSTRACT

A distinct cultivar of impatiens plant named Escapade, particularly characterized by its relatively large, deep orange-red flowers, rounded flowers with petals overlapping, solid green leaves with no variegation, early flowering, reddish purple stems, and its floriferous habit.

1 Drawing Sheet

The present invention relates to a new and distinctive cultivar of Impatiens plant, botanically known as Impatiens, commercially known as New Guinea Impatiens, and known by the cultivar name Escapade. Escapade was developed by me through controlled breeding by crossing the cultivar Morio (U.S. Plant Pat. No. 6,762) (seed parent) with Mikkelsen Seedling No. 89-581-3 (pollen parent).

Asexual reproduction by terminal or stem cuttings has shown that the unique features of this new impatiens are stabilized and are reproduced true to type in successive propagations.

The following combination of characteristics distinguish Escapade from both its parent varieties and other cultivated impatiens of this type known and used in the floriculture industry. The characteristics of Escapade are described with reference to the female parent Morio and the comparison cultivar Zenith, disclosed in U.S. Plant Pat. No. 5,804.

1. Escapade has bright orange-red (34A) flowers somewhat similar to Morio but deeper orange than Zenith (40A fading to 33A).
2. Escapade has a large flower, averaging 6.0 to 6.5 cm in diameter, with Zenith being 5.5 to 6.0 cm in diameter and Morio being 5.0 to 5.5 cm in diameter.
3. The flower of Escapade is very rounded, with all five petals overlapping each other, while the flowers of both Morio and Zenith have an open gap between the two wing petals and the standard.
4. Escapade has a reddish flower spur with a green tip, similar to Zenith, while Morio has a reddish purple spur with an even deeper tip.
5. Both Zenith and Morio have green leaves with heavy cream variegation around the midrib. The leaves of Escapade are solid green.
6. All three cultivars have a similar leaf length (11.0 to 12.0 cm) but Escapade has the broadest leaf at 4.0 to 4.5 cm, compared to Zenith at 3.5 to 4.0 cm and Morio at 3.0 to 3.5 cm, for an average mature leaf.
7. Escapade is 7 to 10 days earlier to bloom than either Morio or Zenith.
8. Escapade is taller at 20 to 22 cm than Zenith at 16 to 18 cm but not as tall as Morio at 25 to 27 cm.
9. Escapade and Zenith have a green midrib and venation on underside of leaves while Morio has a reddish midrib and venation on underside of leaves.
10. Escapade has reddish purple stems that are intermediate between Zenith, which has green stems with a touch of red near internodes, and Morio which has deeper reddish purple stems.
11. Flower pedicels of Escapade and Zenith are greenish with a touch of red while Morio has reddish purple pedicels.

The accompanying color photograph in a front perspective view illustrating the overall appearance of Escapade, with the colors being as true as it is reasonably possible to obtain in a colored reproduction of this type. The photograph was taken on Apr. 15, 1991 under natural light on an overcast day, under double poly greenhouse covering at Ashtabula, Ohio.

The following is a detailed description of my new cultivar, based on plants produced in greenhouses in Ashtabula, Ohio during the Fall and early Winter seasons of the year. Plants were grown in 10 cm pots and measurements were taken 12 weeks after rooted cuttings were planted. Height measurements were taken from the soil line of the container. The plants were grown at 65°-68° F. night temperatures, under 3000-4000 foot candles of light, and at nutritional levels of 250 ppm nitrogen, 75 ppm potassium, and 250 ppm phosphorus, with trace elements added. Habit of growth, foliage coloration, leaf variegation, size of leaves and flower size will be influence by nutritional and environmental conditions, without, however, any variation in the phenotype.

Color references are made to The Royal Horticultural Society Colour Chart except where general terms of ordinary dictionary significance are used.

Parentage: A controlled cross between female parent Morio and male parent Mikkelsen Seedling No. 89-581-3.

Propagation:

A. *Type cutting.*—Stem tip 15 mm long will develop to 4 to 5 cm long in 18 to 21 days.

B. *Time to root.*—8 to 10 days at 23° C. summer; 10 to 12 days at 20° C. winter.

C. *Rooting habit.*—Heavy, fibrous.

Plant description:

A. *Form and habit of growth.*—Mounded, highly self-branched; semi-tall in height; flowers over the top of leaf canopy; continuous flowering, vigorous growing flowering herb.

B. *Foliage description.*—Yellow green leaves with slight reddish purple cast to midrib; no leaf variegation; bottom of leaf is green. 1. Size: 11.0 to 12.0 cm long and 3.5 to 4.0 cm wide for averaging mature leaf. 2. Shape: Lanceolate to ovate with acuminate apex and acute base. 3. Texture: Both upper and lower surfaces are glabrous. 4. Margin: Entire with fine ciliate. 5. Color: young foliage, top side 146A. under side 146B. mature foliage, top side 147A. under side 147B. 6. Venation: Pinnate, green in color.

Flowering description:

A. *Flowering habits.*—Flowers continuously from leaf whorl of 3 to 4 leaves in a progressively orderly manner with usually one flower per leaf axil. However, some will have two flowers per leaf axil. All first flowers in a whorl open before the second flower in the leaf axil of that whorl start to open. When the last flower in a leaf axil opens the first flower in the leaf whorl above starts to open. It takes 5 to 7 days for a mature bud to fully open and then the flower may last two weeks or longer, depending on the environment.

B. *Natural flowering season.*—Indeterminant and continuous, quantity of flowering increases with increasing levels of light.

C. *Flower buds.*—Ellipsoidal, flowers perfect; reddish spur 3.0 to 3.5 cm on mature bud with green tip; throat behind ovary and originating from major sepal.

D. *Flowers borne.*—On individual pedicels mostly green in color with slight reddish tint from whorl of 3 to 4 leaves, flowering progressively around the whorls as buds and leaves develop. Leaf axils usually have one flower bud.

E. *Quantity of flowers.*—Very floriferous because of highly self-branched habit and long-lasting characteristics of flowers.

F. *Diameter of flower.*—6.0 to 6.5 cm.

G. *Petals.*—1. Shape: Heart, with standard being largest. 2. Color: Top side in Fall when opening, 34A with no fading; underside 34B. 3. Number of petals: 5. 4. Size of petals: Standard: 2.5 cm long by 5.5 cm wide; two equal lobes, shallow cut. Wings: 2.75 cm long by 4.0 cm wide; two unequal lobes, moderate cut. Keel: 2.75 cm long by 4.0 cm wide; two unequal lobes, moderate cut.

H. *Reproductve organs.*—1. Stamens: Five (5) in number. a. Anther shape: Hooded, color white with reddish cast. b. Pollen color: Cream. 2. Pistils: a. Stigma shape: Five segmented column, color white. b. Style color: White. c. Ovaries: Five (5) in number, size 5 mm when mature, color green.

*Disease resistance.*—No significant disease or insect problems to date.

Other important characteristics

1. Escapade has demonstrated the ability to tolerate both high temperatures and sunlight and continue to bloom, as well as cool temperatures (40°-50° F.). Thus, growing season outdoors can be expanded.
2. Self-branching, early flowering and top flowering characteristics allow Escapade to be grown in 10 cm pots. However, Escapade is vigorous so that it can be grown in 15 to 25 cm containers as well.

I claim:

1. A new and distinct impatiens plant named Escapade, as illustrated and described.

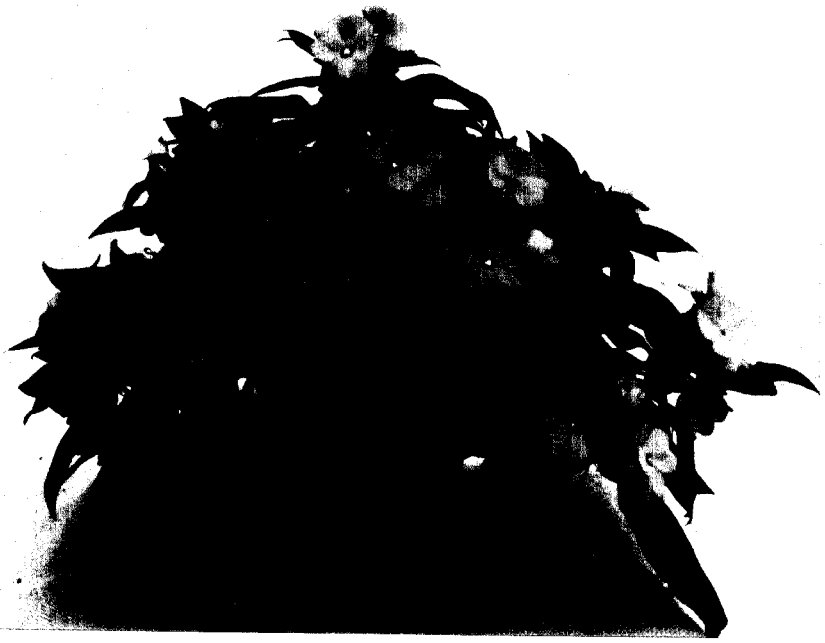

* * * * *